United States Patent [19]

Arnette

[11] Patent Number: 6,098,204
[45] Date of Patent: Aug. 8, 2000

[54] SKI GOGGLES FOR USE WITH AN INSULATING HOOD

[75] Inventor: Gregory F. Arnette, South Laguna Beach, Calif.

[73] Assignee: Arnette Optical Illusions, Inc., San Clemente, Calif.

[21] Appl. No.: 08/537,977

[22] Filed: Oct. 2, 1995

Related U.S. Application Data

[63] Continuation-in-part of application No. 29/020,445, Mar. 24, 1994, Pat. No. Des. 364,181.

[51] Int. Cl.[7] .......................................................... A61F 9/02
[52] U.S. Cl. ........................................ 2/426; 2/452; 2/202
[58] Field of Search ................................ 2/426, 427, 431, 2/435, 436, 437, 439, 440, 441, 447, 448, 173, 202, 203, 204, 205, 428, 429, 430, 432, 433, 434, 438, 442, 443, 444, 445, 446, 449, 450, 451, 452, 4; D16/300, 311

[56] References Cited

U.S. PATENT DOCUMENTS

| D. 222,523 | 11/1971 | Simpkins et al. | D2/234 |
|---|---|---|---|
| D. 224,483 | 8/1972 | Crestin-Billet | D2/234 |
| D. 242,666 | 12/1976 | Smith | D2/234 |
| D. 273,819 | 5/1984 | Yehl | D2/234 |
| D. 327,696 | 7/1992 | Bolle | D16/102 |
| D. 364,181 | 11/1995 | Arnette | D16/312 |
| 2,886,819 | 5/1959 | Uphoff | 2/438 |
| 3,722,985 | 3/1973 | Laliberte et al. | 350/311 |
| 3,885,558 | 5/1975 | Belkin | 2/173 |
| 3,945,044 | 3/1976 | McGee et al. | 2/14 H |
| 4,447,914 | 5/1984 | Jannard | 2/432 |
| 4,556,995 | 12/1985 | Yamamoto | 2/439 |
| 4,823,407 | 4/1989 | Phillips, Jr. et al. | 2/202 |
| 5,018,223 | 5/1991 | Dawson et al. | 2/436 |
| 5,091,996 | 3/1992 | Kirby | 2/206 |
| 5,300,963 | 4/1994 | Tanaka | 351/44 |
| 5,689,834 | 11/1997 | Wilson | 2/436 |

OTHER PUBLICATIONS

"UVEX"—Ad in Skiing, Sep. 1986, p. 43.
Goggles, ad from Skiing, Sep. 1986, p. 159.
Bausch & Lomb ad from Accessories Distributors 1975 Catalog, p. 28.

*Primary Examiner*—Michael A. Neas
*Attorney, Agent, or Firm*—Katherine McGuire; Craig E. Larson

[57] ABSTRACT

Goggles for use in cold weather, high speed outdoor sports, in conjunction with an insulating hood having a facial opening, are configured to receive the hood around the facial opening, to prevent the hood from obstructing the wearer's vision. The goggles are preferably configured with an outer frame incorporating a lens, an inner frame bearing against the wearer's face, with the outer and inner frames spaced apart to receive the hood at least partially around the facial opening. With the present invention it is possible to remove the insulating hood without displacing the goggles from the wearer's face. In the prior art, it was necessary to remove or otherwise displace the goggles, to allow removal or adjustment of the insulating hood.

9 Claims, 2 Drawing Sheets

SKI GOGGLES FOR USE WITH AN INSULATING HOOD

CROSS-REFERENCE TO RELATED APPLICATION

This application is a continuation-in-part of Ser. No. 29/020,445, filed Mar. 24, 1994 now U.S. Pat. No. Des. 364,181.

FIELD OF THE INVENTION

The present invention relates generally to eye protection devices used in practicing active outdoor sports, and more particularly to goggles for use by participants in high speed, cold weather sports, where an insulating hood is also worn.

BACKGROUND OF THE INVENTION

Protective eyewear for use in practicing active outdoor sports where participants are traveling at considerable velocities is well known. It is important to protect the participant's eyes from direct exposure to uncomfortably high "winds" as well as small particles such as dust, insects and rocks which may be suspended in the air. In cold weather sports such as skiing, snowboarding or snowmobiling, it is additionally important to shield the wearer's face and eyes as much as practical from snow and dangerous wind chill and to cover the wearer's head to prevent rapid heat loss. Typically, insulating hoods are worn which cover the head and neck while providing an opening for the participant's face around the eyes, nose and mouth. The participant first dons the hood and adjusts the position of the facial opening to provide unobstructed vision and breathing. Then the goggles are placed over the hood such that the goggles hold down the edge of the hood facial opening so as to keep the hood clear of the wearer's eyes. The length of the strap around the wearer's head is adjusted, and it is usually necessary to further adjust the position of the frames on the wearer's face, such that the goggles may be securely and comfortably worn.

Oftentimes it is desirable to stop and momentarily remove the hood or otherwise allow air inside the hood, such as if the wearer becomes warm or is perspiring. To do so, it is necessary to first entirely remove the goggles or pull the goggles away from one's face, such that the hood may be moved around. Then prior to resuming skiing, snowboarding, snowmobiling and the like, the hood and goggles are put back into place and readjusted. As can be appreciated, it is a nuisance to repeatedly go through the motions with one or both hands of first removing the goggles, then removing the hood, and reversing the steps prior to resuming a sports activity. Some prior art devices have included goggles and hoods integrated together, but such goggle and hood portions must be removed and replaced together or positively detached from each other prior to separate removal.

Accordingly, it is desirable to provide a sports goggle configured to be worn with an insulating hood, such that a participant is able to remove or adjust the hood without removal or displacement of the goggles. Additionally, the sports goggle should still serve the function of positioning and holding the hood around the wearer's eyes.

SUMMARY OF THE INVENTION

The present invention specifically addresses and alleviates the above-mentioned deficiency associated with the prior art, that the goggles must be removed or otherwise pulled away from the wearer's face to remove and/or adjust the position of the hood. The present invention comprises generally goggles especially configured to receive the hood at least partially around the facial opening of the hood, such that the hood is held in place by the goggles and such that the hood may be removed without displacing the goggles.

More particularly, the present invention comprises goggles having an outer frame with a lens disposed therein, and having an inner frame connected to the outer frame, the inner frame bearing against the wearer's face. The outer and inner frames are spaced apart along at least a portion of the perimeter of the goggles, the space configured to receive the hood around a corresponding portion of the facial opening of the hood. The outer and inner frames are preferably spaced apart at the outboard and upper edges of the goggles. Thus, the facial opening of the hood is retained around the upper and outboard edges of the goggles, keeping the hood out of the wearer's eyes while preventing cold air from reaching surrounding portions of the wearer's head and face.

In a preferred embodiment, the spaced-apart outer and inner frames are held together by a flexible web operative to reduce the transmission of shock loads from the outer frame. In the preferred embodiment, the flexible web further includes a plurality of apertures to allow air flow between the lens and the wearer's face. This necessary ventilation helps alleviate fogging and the forming of condensation on the inside surface of the lens, which dangerously acts to impair the wearer's vision. The apertures are preferably covered by a tight mesh material which prevents the entry of small particles while still permitting necessary air flow.

These, as well as other advantages of the present invention will become more apparent from the following description and drawings. It is understood that changes in the specific structure shown and described may be made within the scope of the claims without departing from the spirit of the invention.

DETAILED DESCRIPTION OF THE PREFERRED EMBODIMENT

The detailed description set forth below in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is understood, however, that the same or equivalent functions and sequences may be accomplished by different embodiments that are also intended to be encompassed within the spirit and scope of the invention.

Figure 1:
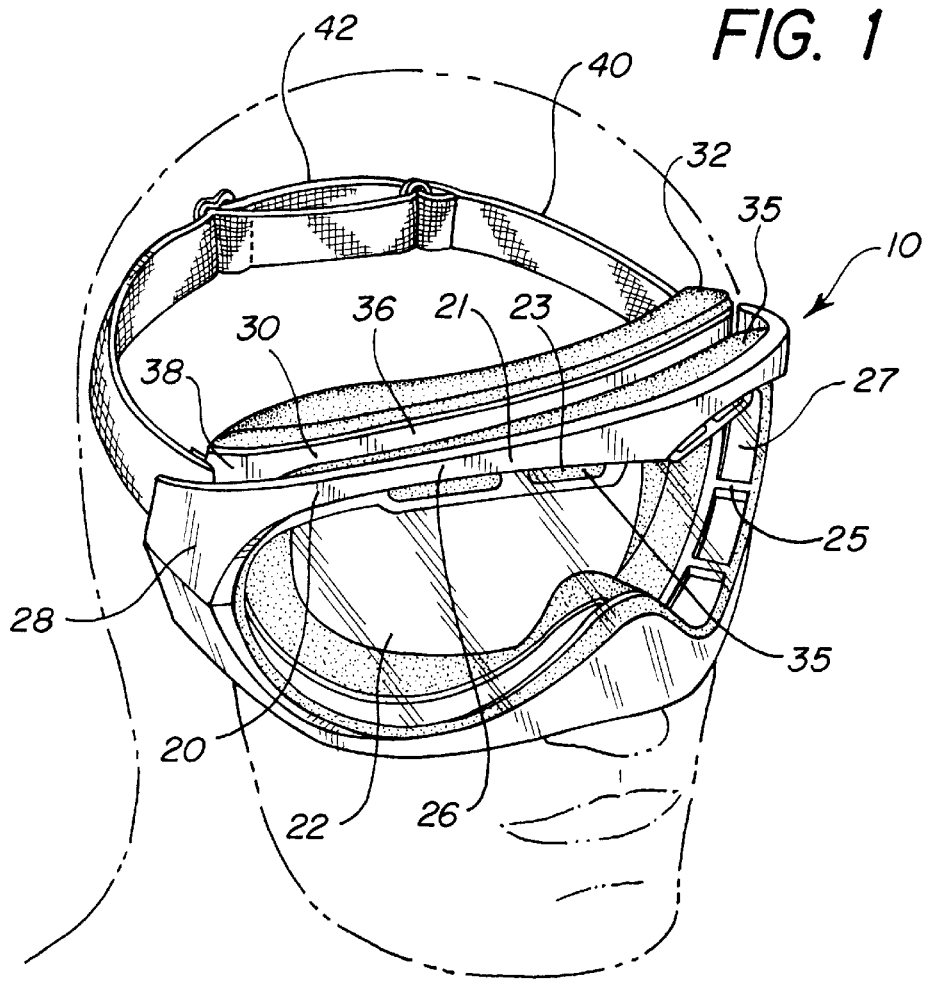
FIG. 1 is a perspective view of the goggles of the present invention as worn by a participant.
Figure 2:
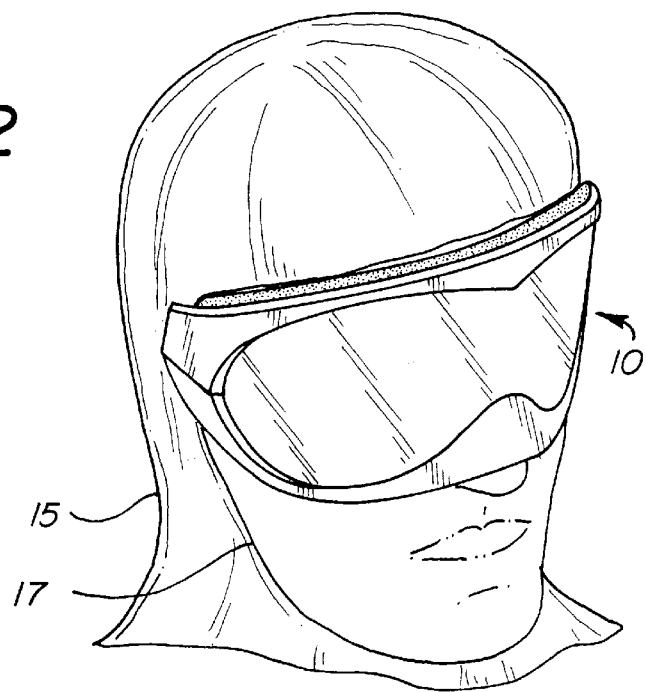
FIG. 2 is a perspective view of the goggles as integrated with an insulating hood.

The goggles of the present invention are illustrated in FIGS. 1–4 which depict a presently preferred embodiment of the invention. Referring now to FIGS. 1 and 2, a cold weather, high speed sports participant is shown wearing the goggles 10 and additionally shown wearing an insulating hood 15 (FIG. 2) covering the wearer's head but having a facial opening 17. Rather than the goggles 10 and the strap 40 fitting over the hood 15 as is conventional, the goggles 10 and strap 40 fit below the hood 15 with the goggles 10 configured to receive the hood 15 around the facial opening 17. This offers the significant advantage of enabling the wearer to remove the hood 15 without displacing the goggles 10.

Figure 3:
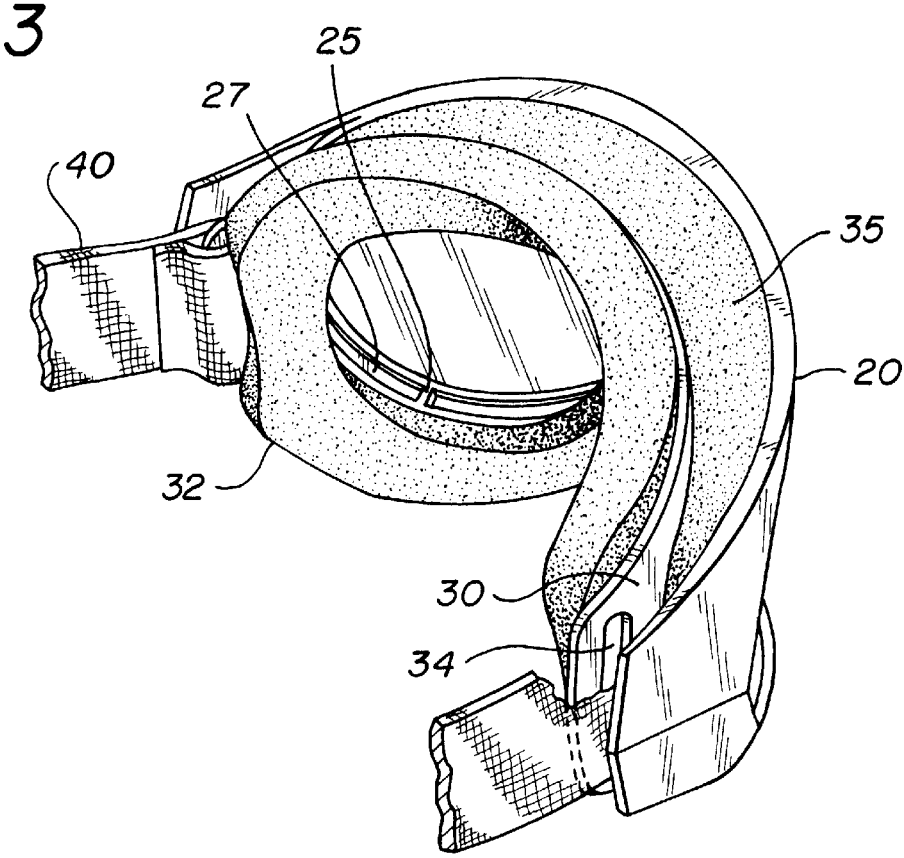
FIG. 3 is a reverse angle perspective view of the goggles of the present invention.

Now also referring to FIG. 3, the goggles 10 of the preferred embodiment of the present invention may be further described. The goggles 10 include an outer frame 20 which holds a preferably darkly tinted lens 22, and an inner frame 30 including a cushion 32 which bears against the wearer's face. The outer and inner frames 20 and 30 are of a curved shape to conform to the wearer's face, as well as to form an aerodynamic surface for smooth air flow across and around the goggles 10. The outer and inner frames 20 and 30 additionally are sufficiently flexible, in combination with adjustment means 42 of the strap 40, to accommodate size and shape variations among wearer's faces and heads. The outer frame 20 and inner frame 30 are spaced apart but connected by a flexible web 25 around the perimeter of the goggles 10, the flexible web 25 having a plurality of apertures 27. The flexible web 25, while tying together and maintaining the connection between the outer and inner frames 20 and 30, bends and deflects so as to reduce the impact of forces which may impact the outer frame 20 caused by, for example, bumping into things. The outer frame 20, inner frame 30, and flexible web 25 are all preferably constructed as a single piece of a thin molded plastic material. Overlying the apertures 27 of the flexible web 25 is a tightly meshed cover 35, which prevents small particles or debris from entering the apertures 25 while still allowing air to flow therethrough. The goggles 10, outer frame 20 and lens 22 are preferably configured to allow convenient, easy removal and replacement of the lens 22, in the event it becomes scratched, cracked or otherwise damaged. The lens 22 around the perimeter may include small notches (not shown) to ensure correct alignment of the lens 22 in their installation into the outer frame 20. The outer frame 20 may optionally be configured with a pair of spaced apart lenses 22, known as double lenses, to form an air chamber between the lenses 22 in a further attempt to eliminate fogging and forming of condensation on the lenses 22. To accommodate mounting of the double lenses 22 the outer frame 20 includes a tab 21, and to create the air chamber through the outer frame 20, tab 21 and the double lenses 22 are a plurality of apertures 23. The cover 35 preferably extends, from between the upper edges 26 and 36 of the outer and inner frames 20 and 30, to between one of the lenses 22 and the tab 21. This allows air flow through the apertures 23, but prevents the entry of small particles or debris between the lenses 22.

Figure 4:
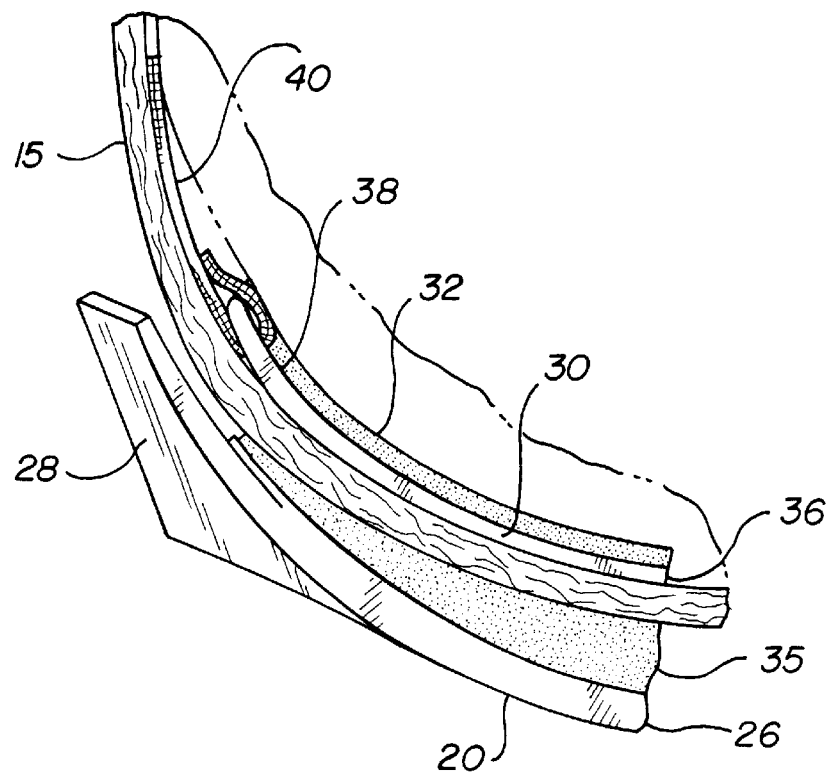
FIG. 4 is a top view of the right side outboard edge of the goggles as integrated with the hood.

Next, the operation, function, and use of the goggles 10 of the preferred embodiment of the present invention may be described. In the prior art, a cold weather, high speed sports participant would first don the insulating hood 15 and adjust the facial opening 17 so as not to obstruct vision around the eyes and/or breathing through the nose and mouth. Then, the goggles 10 including the strap 40 would be put on over the hood 15 around the facial opening 17 so as to hold that portion of the hood 15 in place. If it was desirable to remove or adjust the hood 15, it was necessary to first remove or displace the goggles 10 from the wearer's face. The goggles 10 of the present invention can still be used in that conventional manner, but the goggles 10 may additionally be worn underneath the hood 15 with the perimeter of the hood 15 facial opening 17 being held between the outer and inner frames 20 and 30 between the upper edges 26 and 36 and the outboard edges 28 and 38 respectively (as shown in FIGS. 2 and 4). In this way, the hood 15 may be easily removed and/or adjusted without removing or displacing the goggles 20. Although the hood 15 facial opening 17 is placed between the goggles 10 outer and inner frame 20 and 30 it is not positively restrained there. This offers an important safety benefit that if the hood 15 gets caught on something it is easily separated from the goggles 10.

It is understood that the goggles described herein and shown in the drawings represent only a presently preferred embodiment of the invention. Indeed, various modifications and additions may be made to such embodiment without departing from the spirit and scope of the invention. These and other modifications and additions may be obvious to those skilled in the art and may be implemented to adapt the present invention for use in a variety of different applications.

What is claimed is:

1. Goggles to protect a wearer's eyes, the wearer additionally wearing a hood covering the wearer's head, the hood having a facial opening over the wearer's face, the goggles comprising:

an outer frame having opposite outboard edges and an upper edge extending between said outboard edges;

an inner frame having opposite outboard edges and an upper edge extending between said inner frame outboard edges, said inner and outer frames being interconnected with said inner frame bearing against the wearer's face; and a strap attached to and extending between said inner frame outboard edges, said strap adapted to extend behind the wearer's head to hold the goggle on the wearer's face;

said inner frame outboard and upper edges being aligned with and spaced from said outer frame outboard and upper edges respectively, thereby forming an uninterrupted channel extending between said opposite outboard edges and along said upper edges of said inner and outer frames, whereby a part of said hood perimeter may extend into the entire length of said channel such that said part of said hood perimeter and said inner frame together create a barrier against air and dust entering the wearer's hood and goggle, and whereby the hood may be alternately removed and replaced upon the wearer's head without moving the goggles on the wearer's head.

2. The goggle of claim 1, wherein said outboard edges of said inner and outer frames extend substantially parallel to each other.

3. The goggle of claim 2, wherein said outboard edges of said inner and outer frames are curved to conform to the wearer's face.

4. The goggle of claim 2, wherein the hood perimeter lies against the upper and outboard edges of said inner frame.

5. The goggles of claim 1 wherein the spaced apart outer and inner frames are connected by a flexible web, to reduce shock loads from the outer frame to the inner frame.

6. The goggles of claim 5 wherein the flexible web includes a plurality of apertures to allow air flow between the lens and the wearer's face.

7. The goggles of claim 6 wherein the web apertures are covered with a material preventing entry of particles while still allowing air flow.

8. The goggles of claim 1 wherein the inner frame includes a cushion disposed between the goggles and the wearer's face.

9. A method of protecting a cold weather, high speed sports participant's eyes and head from direct exposure to the wind and particles suspended in the air, the method comprising the steps of:

(a) placing goggles over the participant's eyes, said goggles comprising:
   an outer frame having a lens disposed therein;
   an inner frame connected to the outer frame, the inner frame bearing against the wearer's face; and
   a strap connected to the inner frame outboard edges;
   the outer and inner frames spaced apart at their outboard edges to receive and hold a hood such that the hood is held in place by the goggles and such that the hood may be removed without displacing the goggles;

(b) securing the goggles with the strap extending around the back of the participant's head;

(c) placing a hood over the participant's head; and (d) adjusting the perimeter of the facial opening of the hood to lie between the outboard edges of the outer and inner frames of the goggles.

* * * * *